US009149333B2

(12) United States Patent
Harschack et al.

(10) Patent No.: US 9,149,333 B2
(45) Date of Patent: Oct. 6, 2015

(54) ENDOLUMINAL LASER ABLATION DEVICE AND IMPROVED METHOD FOR TREATING VEINS

(75) Inventors: Alexander Harschack, Bad Honnef (DE); Wolfgang Neuberger, Dubai (AE)

(73) Assignee: Biolitec Pharma Marketing Ltd, Labuan (MY)

( * ) Notice: Subject to any disclaimer, the term of this patent is extended or adjusted under 35 U.S.C. 154(b) by 415 days.

(21) Appl. No.: 12/895,488

(22) Filed: Sep. 30, 2010

(65) Prior Publication Data

US 2011/0282330 A1 Nov. 17, 2011

Related U.S. Application Data

(63) Continuation-in-part of application No. 12/731,525, filed on Mar. 25, 2010.

(51) Int. Cl.
*A61B 18/18* (2006.01)
*A61B 18/24* (2006.01)
*A61B 17/22* (2006.01)
*A61B 18/22* (2006.01)

(52) U.S. Cl.
CPC ............ *A61B 18/24* (2013.01); *A61B 17/22012* (2013.01); *A61B 2018/2272* (2013.01)

(58) Field of Classification Search
CPC ....... A61B 18/24; A61B 18/22; A61B 18/245
USPC ...................... 128/898; 606/2–19; 607/88–94
See application file for complete search history.

(56) References Cited

U.S. PATENT DOCUMENTS

| 5,057,106 | A | * | 10/1991 | Kasevich et al. | 606/33 |
|---|---|---|---|---|---|
| 5,242,438 | A | * | 9/1993 | Saadatmanesh et al. | 606/15 |
| 5,292,320 | A | * | 3/1994 | Brown et al. | 606/15 |
| 5,303,324 | A | * | 4/1994 | Lundahl | 385/147 |
| 5,509,917 | A | * | 4/1996 | Cecchetti et al. | 606/15 |
| 5,562,657 | A | * | 10/1996 | Griffin | 606/17 |
| 5,578,029 | A | * | 11/1996 | Trelles et al. | 606/25 |
| 6,398,777 | B1 | * | 6/2002 | Navarro et al. | 606/7 |
| 6,620,153 | B2 | * | 9/2003 | Mueller et al. | 606/15 |

(Continued)

OTHER PUBLICATIONS

Endovenous Laser Treatment for Primary Varicose Veins; Van den Bussche et al., Acta Chir belg, 2006, 106, 32-35.*

*Primary Examiner* — William Thomson
*Assistant Examiner* — John R Downey
(74) *Attorney, Agent, or Firm* — BJ Associates; Bolesh J. Skutnik (57) ABSTRACT

Methods and devices are provided for efficient low power density endoluminal treatment of veins. Devices emit energy radially from an optical fiber with two or more emitting portions at its distal region. for 360° radial (circumferential) emission of vein walls. Emitting sections comprise a fiber with a truncated cone attached to a short conically-tipped fiber at the distal end. The fiber segments are butt-coupled or glued, and then laterally fused to the protective glass dome/ cap. Laser power is substantially entirely absorbed within a fraction of the blood vessel wall to achieve blood vessel closure. Wavelengths including 980 nm, 1470 nm and 1950 nm are used which are substantially absorbed within the first third of a blood vessel wall. Consequently, a local anesthetic along the treated blood vessel is substantially avoided. Due to a fiber device's multiple emission points, withdrawal speed can be increased, and/or emitted energy levels can be set at minimum values.

19 Claims, 6 Drawing Sheets

(56) References Cited

U.S. PATENT DOCUMENTS

| | | | |
|---|---|---|---|
| 6,964,661 B2* | 11/2005 | Rioux et al. | 606/41 |
| 6,986,766 B2* | 1/2006 | Caldera et al. | 606/15 |
| 2004/0092913 A1* | 5/2004 | Hennings et al. | 606/3 |
| 2005/0015123 A1* | 1/2005 | Paithankar | 607/88 |
| 2005/0131400 A1* | 6/2005 | Hennings et al. | 606/15 |
| 2006/0217692 A1* | 9/2006 | Neuberger | 606/12 |
| 2008/0065058 A1* | 3/2008 | Neuberger | 606/15 |
| 2008/0194973 A1* | 8/2008 | Imam | 600/478 |

* cited by examiner

ENDOLUMINAL LASER ABLATION DEVICE AND IMPROVED METHOD FOR TREATING VEINS

CROSS REFERENCE TO PRIORITY APPLICATION

This patent application is a continuation in part and claims priority to, U.S. Pat. No. 12/731,525, filed Mar. 25, 2010, by Wolfgang Neuberger entitled "Endoluminal Laser Ablation Device And Method For Treating Veins", which in turn was based on U.S. Pat. No. 12/395,455, filed Feb. 27, 2009, by Wolfgang Neuberger entitled "Endoluminal Laser Ablation Device And Method For Treating Veins", which in turn was based on U.S. provisional patent application No. 61/104,956, filed Oct. 13, 2008, entitled "Radial Emitting Device And Method For Treating Veins", U.S. provisional patent application No. 61/079,024, filed 8 Jul. 2008, and U.S. provisional patent application No. 61/067,537, filed 28 Feb. 2008, entitled "Rapid Insertion Device and Method For Improved Vascular Laser Treatment", each of which is hereby expressly incorporated by reference in its entirety as part of the present disclosure.

BACKGROUND OF THE INVENTION

1. Field of the Invention

The present invention relates to laser systems for medical treatments and in particular, for laser surgical procedures. More particularly, it relates to optical fiber systems and methods used for the treatment of various medical conditions, including venous insufficiency.

2. State of the Art Disclosure Statement

There are a number of human medical conditions in which it is necessary to apply energy to hollow structures of the body from the inside. One of those conditions is venous insufficiency. The human venous system of the lower limbs consists essentially of the superficial venous system and the deep venous system, both connected by perforating veins. The superficial system comprises the great and the small saphenous veins, while the deep venous system includes the anterior and posterior tibial veins, which converge to form the popliteal vein near the knee. The popliteal vein, in turn, becomes the femoral vein when joined by the small saphenous vein.

The venous system comprises valves that function to achieve unidirectional blood flow back to the heart. Venous valves are bicuspid valves wherein each cusp forms a blood reservoir. The bicuspid venous valves force their free surfaces together under retrograde blood pressure. When properly operating, retrograde blood flow is prevented, allowing only antegrade flow to the heart. A bicuspid valve becomes incompetent when its cusps are unable to seal properly under a retrograde pressure gradient such that retrograde blood flow occurs. When retrograde blood flow occurs, pressure increases in the lower venous sections which can, in turn, dilate veins and lead to additional valvular failure.

Valvular failure, usually referred to as venous insufficiency, is a chronic disease that can lead to skin discoloration, varicose veins, pain, swelling and ulcerations. Varicose veins are blood vessels that have become enlarged and twisted and have progressively lost elasticity in their walls. Due to the widening of the blood vessels, the valves cannot be completely closed and the veins lose their ability to carry blood back to the heart. This leads to an accumulation of blood inside the vessels which can, in turn, further enlarge and twist the veins. Varicose veins usually have a blue or purple color and may protrude in a twisted form above the surface of the skin giving rise to a characteristically unattractive appearance. Varicose veins are commonly formed in the superficial veins of the legs, which are subject to high pressure when standing. Other types of varicose veins include venous lakes, reticular veins and telangiectasias.

There are a number of treatments available for eradicating these types of vascular pathologies. Varicose veins are frequently treated by eliminating the insufficient veins. These treatments force the blood that otherwise would flow through the eliminated vein to flow through the remaining healthy veins. Various methods can be used to eliminate problematic insufficient veins, including surgery, sclerotherapy, electrocautery, and laser treatments.

Endoluminal laser ablation ("ELA") is a modern minimally invasive technique that is increasingly preferred over surgery, sclerotherapy and electro-cautery approaches for treatment for varicose veins. This is mainly due to the optimal results with minimum undesired side effects obtained in comparison to other methods used. In a typical prior art ELA procedure, an optical fiber is introduced through an introducer sheath into the vein to be treated. An exemplary prior art ELA procedure includes the following steps: First, a guide wire is inserted into the vein to be treated, preferably with the help of an entry needle. Second, an introducer sheath is introduced over the guide wire and advanced to a treatment site. Then, the guide wire is removed leaving the introducer sheath in place. The optical fiber (coupled to a laser source) is then inserted through the introducer sheath and positioned so that the flat emitting face at the distal tip of the fiber and the sheath are at the same point. Often local anesthesia is then applied to the tissue surrounding the vein to be treated. Prior to lasing, the sheath is pulled back from the flat emitting face a distance sufficient to prevent the emitted laser energy from damaging the sheath. Then, the laser is fired to emit laser energy through the flat emitting face and into the blood and/or vein wall directly in front of the emitting face. While the laser energy is emitted, the laser fiber and introducer sheath are withdrawn together to treat and close a desired length of the vein. The laser energy is absorbed by the blood and/or vein wall tissue and, in turn, thermally damages and causes fibrosis of the vein.

U.S. Pat. No. 6,200,332 to Del Giglio discloses an exemplary prior art device and method for under skin laser treatment with minimal insertions into the area of treatment. Common vascular abnormalities such as capillary disorders, spider nevus, hemangioma, and varicose veins can be selectively eliminated. A needle is inserted into the vascular structure and the targeted abnormalities are subjected to emitted laser radiation. The device allows for orientation and positioning of the laser delivering optical fiber during treatment. Infiltrated anesthesia is generally not necessary. An extension piece maintains the optical fiber in a fixed position relative to, and at a fixed distance from, a hand piece to allow the user to know the extent to which the fiber has been inserted into the vein.

U.S. Pat. No. 6,398,777 to Navarro et al. describes another ELA procedure in which percutaneous access into the vein lumen is obtained using an angiocatheter through which a fiber optic line is introduced. The fiber optic line has a bare, uncoated tip defining a flat radiation emitting face. The '777 patent teaches manually compressing the vein, such as by hand or with a compression bandage, to place the vein wall in contact with the flat emitting face of the fiber tip. The laser energy is delivered in high energy bursts into the portion of the vein wall in contact with the bare fiber tip. The wavelength of the laser energy is in the range from about 532 nm to about 1064 nm and the duration of each burst is about 0.2 seconds to about 10 seconds. Each burst delivers from about 5 watts to about 20 watts of energy into the vein wall. The '777 patent and other prior art ELA procedures teach delivering sufficient energy to insure damage to the entire thickness of the vein wall to ultimately result in fibrosis of the vein wall and occlusion of the greater Saphenous vein.

Consistent with the '777 patent, the prior art teaches applying relatively high energy levels (e.g., ≥80 J/cm) in order to improve the treatment success of ELA of incompetent Saphenous veins. Timperman et al. teach that endovenous laser treatments of the Saphenous vein are particularly successful when doses of more than 80 J/cm are delivered. Timperman et al. collected data regarding the length of treated vein and the total energy delivered on 111 treated veins. The wavelength of laser energy applied was 810 nm or 940 nm. Of the 111 treated veins, 85 remain closed (77.5%) during the follow-up period. In this group of successfully treated veins, the average energy delivered was 63.4 J/cm. For the 26 veins in the failure group, the average energy delivered was 46.6 J/cm. No treatment failures were identified in patients who received doses of 80 J/cm or more. P. Timperman, M. Sichlau, R. Ryu, "Greater Energy Delivery Improves Treatment Success Of Endovenous Laser Treatment Of Incompetent Saphenous Veins", Journal of Vascular and Interventional Radiology, Vol. 15, Issue 10, pp. 1061-1063 (2004).

One drawback associated with this and other prior art ELA treatments is that the laser radiation is applied only through the very small flat emitting face at the bare fiber tip. As a result, substantially only a very small, localized portion of the blood and/or vein wall in front of the flat emitting face directly receives the emitted laser energy at any one time. Yet another drawback of such prior art ELA devices and methods is that the laser radiation is directed only in a forward direction out of the flat emitting face of the fiber. Accordingly, substantially no radiation is emitted radially or laterally from the fiber tip thereby delivering the laser radiation in a relatively localized manner. A further drawback is that the relatively high levels of energy delivered into the vein create significantly increased temperatures which can, in turn, give rise to corresponding levels of pain in the surrounding tissues. The relatively high levels of energy delivered also can give rise to corresponding levels of thermal damage in surrounding tissues. The more intense the thermal damage, the greater is the chance for post procedure pain, bruising and the possibility of paresthesia. Paresthesia is an abnormal and/or unpleasant sensation resulting from nerve injury. Yet another drawback is that such relatively high levels of energy delivery and/or localized concentrations of laser radiation can give rise to vein perforations. As a consequence, such prior art ELA procedures can require relatively high levels of anesthetic, such a local tumescent anesthesia, more time, and can give rise to more stress to both a patient and physician, than otherwise desired. Lower levels of energy can be applied in some cases, if the pullback speed is considerably decreased. However, lowering the speed may still not be enough to cause appropriate vein closure. Furthermore, this would lengthen treatment time considerably and physicians and patients demand progressively shorter treatment times.

A further drawback of prior art ELA treatments is that they employ a tumescent technique involving substantial volumes of anesthesia to create tumescence. For example, a typical prior art ELA treatment, reportedly, employs at least about 100 ml to about 300 ml or more of anesthesia depending on the length of vein to be treated. The anesthesia is injected into the tissue along the length of the vein. In most cases, the anesthesia is injected into a perivenous cavity defined by one or more fascial sheaths surrounding the vein, which requires less volume to create tumescence. In other cases, the anesthesia is injected into the leg tissue surrounding the vein. The anesthesia typically consists essentially of dilute concentrations of Lidocaine and Epinephrine, a vascular restrictor, in a saline solution. One drawback of such techniques is that the anesthetic is toxic, and in some cases when, for example, substantial volumes are employed, the anesthetic can cause adverse patient reactions, such as convulsions. Yet another drawback of the tumescent technique is that patients can experience an undesirable elevation in blood pressure due to the use of Epinephrine. A still further drawback of the tumescent technique is that it requires the injection of substantial volumes of liquid anesthetic along the length of the vein, which adds a significant amount of time to the overall ELA procedure, and can give rise to adverse post treatment side effects, such as black and blue marks, and other adverse effects associated with such large volumes of anesthetic.

Although the tumescent anesthesia or cold saline tumescent infusion used in the tumescent technique of prior art ELA procedures creates a heat sink surrounding the vein, it can still allow for significantly higher levels of thermal damage to the surrounding tissues than desired. The more intense the thermal damage the greater is the chance for post procedure pain, bruising, and the possibility of paresthesia. For example, the significant quantities of tumescent anesthesia employed in prior art ELA procedures typically will prevent a patient from feeling any thermal stimulation of the nerves, and therefore will prevent the patient from alerting the physician to stop or adjust the procedure to prevent undesirable thermal damage. The tibial nerve (TN) and its common peroneal nerve (CPN) branch both are subject to the possibility of such damage. The CPN is very superficial in the lateral leg just below the knee, and thermal damage to this nerve can lead to foot drop. Similarly, the TN is subject to the possibility of thermal damage when exploring high in the popliteal fossa. Depending on its extent, thermal damage to the TN can lead to muscle dysfunction of the calf and foot muscles. The sural nerve (SUN) and Saphenous nerve (SAN) likewise are subject to the possibility of thermal damage when performing ELA of the small Saphenous vein (SSV) or the GSV below the knee. The SUN runs very close to the SSV especially distally closer to the ankle. The SAN runs very close to the GSV below the knee especially, again, distally closer to the ankle. Significant quantities of anesthesia, such as tumescent anesthesia, can unknowingly lead to thermal damage of such nerves.

US Patent Application Publication 2007/0167937 by Brown discloses an apparatus for endovascular techniques for delivering energy to tissue adapted to minimize burn back caused by contact between the apparatus and bodily fluids. Configurations of apparatus include a tip that can be arranged to direct light in a radial direction along an arc extending up to 360 degrees around the fiber.

Mentioned prior art inventions lack the possibility of irradiating a vessel in radial form 360° at multiple emission sections. Physicians and patients prefer short effective treatments with the need for minimum or no anesthesia. Physicians have also expressed the desire for a treatment using minimum energy levels so fiber that has minimum or no chance of being damaged inside treated vessel. There is thus a need for a laser treatment system that improves on the state of the art by providing a better, safe, more robust fiber tool to enhance speed of removal, ease of handling, and eliminate the need for using anesthesia while maintaining the benefits of effective vessel ablation. Present invention addresses this need.

OBJECTIVES AND BRIEF SUMMARY OF THE INVENTION

It is an objective of the present invention to provide a device and method for improved medical laser treatments.

It is another objective of the present invention to treat vascular disorders such as venous insufficiency.

It is yet another objective of the present invention to carry out accurate safe, efficient ablation of vessels, by using a localized energy source and conveying means.

It is also an objective of the present invention to perform treatment of insufficient veins using low power density energy.

It is still another objective of the present invention to perform uniform multipoint radial laser energy to the interior of insufficient veins.

Briefly stated, an improved device and method are provided for safe and efficient low power density endoluminal treatment of venous insufficiency and similar procedures. One such device emits pulsed or continuous energy radially from an optical fiber with two or more emitting portions at its distal region, for 360° radial emission at various portions of the vein. Each emitting section comprises a fiber with a truncated cone and a short fiber segment with a conical tip at the distal end of the fiber. Different embodiments are presented which vary according to geometrical dimensions of emitting sections, such as diameter of the truncated cone, fiber core diameter and length of the fiber segment in front of the fiber with its truncated cone. In a preferred embodiment, the fiber and each short fiber segment are "butt-coupled" inside the glass dome with no additional adhering means. The fiber and the short fiber segment are laterally fused to the protective glass dome. As the back end of the truncated cone section is fused to the outer tube, the area in close contact with the forward piece is fused to the forward section. In another preferred embodiment, the truncated cone of the fiber is glued to the proximal end of the fiber segment. In another embodiment, the contact area is fused, then an outer tube is attached. Laser radiation is transmitted at a wavelength and power such that is it substantially entirely absorbed within a fraction of the blood vessel wall to sufficiently damage the intravascular endothelium and, in turn, achieve blood vessel closure. Such wavelengths include, but are not limited to 980 nm, 1470 nm and 1950 nm. Because the energy is substantially entirely absorbed within the first third of a blood vessel wall, the need for a local anesthetic along the treatment area of the blood vessel is substantially avoided. Because the optical fiber device contains multiple emission points, withdrawal speed can be increased, emitted energy levels can be set at minimum values.

DETAILED DESCRIPTION OF PREFERRED EMBODIMENTS

The present invention provides an improved method and device for fast, safe and effective endoluminal laser ablation ("ELA") that may be performed safely and rapidly at relatively low power densities.

According to prior art, medical laser fibers are generally configured externally concentric to the fiber's main axis, for instance, bare fibers, ball tipped fibers, conical fibers or side-emitting fibers. When used for ELA procedures, these fibers lack efficiency and effectiveness, in comparison to the fibers of the present invention, which emit completely circumferentially with respect to their fiber axis. Another limitation presented by prior art fibers is the emission of energy essentially only at their fiber tip. A faster and more effective treatment can be assured if, in addition to the emission at its fiber tip, additional emission sections are present. It would be even more advantageous if all emission sections emit radially. Thus, the need for anesthesia would be virtually eliminated. The present invention discloses several variants of an energy emitting fiber with multiple radially emitting sections.

US Patent Application US20090240242A1 disclosed by Neuberger which is assigned to the Assignee of the present invention and is hereby incorporated by reference in its entirety as part of the present disclosure, as noted in the priority section, relates to a device that emits pulsed or continuous energy radially through an optical fiber end with a conical shaped tip for 360°radial emission. A conical reflective surface is distally spaced opposite to and faces the emitting tip for enhancing radial emission efficiency by reflecting out any designed or remnant forwardly transmitted energy in radial directions. Laser radiation is transmitted at a wavelength and power such that it is substantially entirely absorbed within the blood vessel wall to sufficiently damage the intravascular endothelium and, in turn, achieve blood vessel closure. Because the energy is substantially entirely absorbed within the blood vessel wall, the need for a local anesthetic along the treatment area of the blood vessel is substantially avoided. One embodiment of this invention presents multi emission sections. The emitting section comprises several regularly-spaced grooves or nicks into the core through the cladding, for achieving radial laser emission along an emission zone. Each groove causes some radiation to be partially emitted sidewise out of the fiber and a portion of radiation transmitted to a subsequent groove, with the majority traveling forward to the distal tip. The distal optical fiber tip defines a conical shape for achieving 360 radial emission, and may include a conical reflective surface axially spaced relative to and oppositely facing the emitting surface for enhancing efficiency and effectiveness of radial emission by reflecting out any designed or remnant forwardly transmitted energy in radial. directions. This device does irradiate completely circumferentially at the distal fiber tip and does allow some additional spots of radiation away from the fiber tip. This structure however with multiple nicks/grooves along the distal end is difficult to manufacture consistently and makes a length of fiber at the distal end particularly vulnerable to fracture during introduction and operation. There remains a need to make a device which does not have these problems.

Present invention relates to an improvement of mentioned device by presence of at least a second circumferential radiating zone, whose strength and integrity are more easily maintained. Furthermore, manufacturing is much better controlled increasing the precision of output from fiber to fiber. This in turn allows practitioners to make more confident use of the multiple/extended exposures to the lasing energy.

Figure 1:
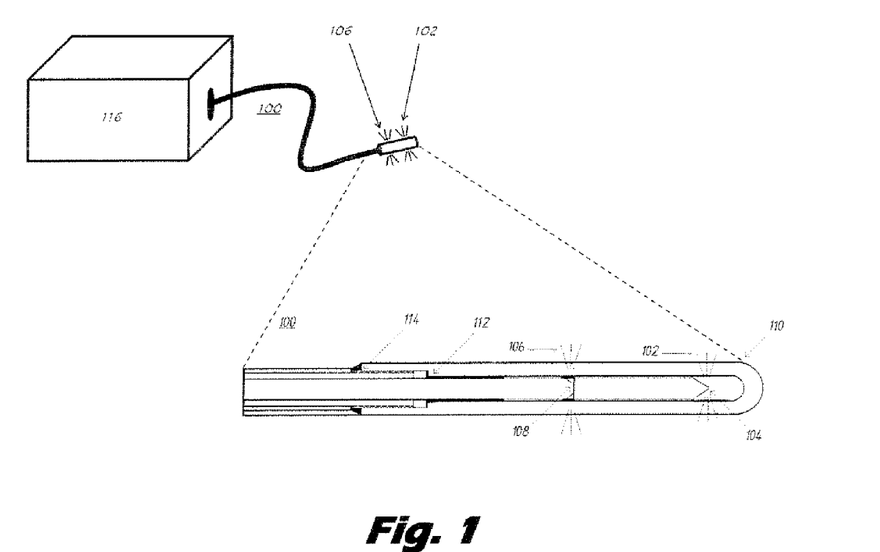
FIG. 1 depicts a preferred embodiment of present invention comprising an optical fiber with two emitting sections optically coupled to a laser radiation source.

FIG. 1 depicts a diagram of a preferred embodiment of present invention comprising optical fiber 100 with two radiation zones, optically connected to laser radiation source 116. First radiation zone 102 emits at cone shaped tip 104 and second radiation zone 106 emits at truncated cone 108. Cap 110 encloses first radiation zone 102 and second radiation zone 106, and is preferably shaped like a glass dome. Thus, the energy distribution between zones is determined by the zone of cap/glass dome 110 diameter. In the same way it is possible to make. three or more radiating zones. The direction of the radiation is determined by the angle of the fiber's conical parts.

The truncated cone 108 of the fiber may or may not be fused with the surface of the end face of the first fiber. When not fused, the gap between them may be filled with glue or with liquid.

The lateral surface of the fibers may be fused or glued to cap/glass dome 110. To exclude the bubble formation, for better fusion process and in order to decrease thermal stress, the fluorine content of the fiber's cladding region can be decreased in direction of the lateral surface down to a certain level or down to zero.

Geometric dimensions can be changed in limits. In a preferred embodiment, the quartz cap diameter is 0.5-3 mm, depending on the fiber dimensions, the length of quartz cap/cover is 5-50 mm and the conical section angle is 50-90°.

Two different glues are used to fix the fiber at the end of the glass dome.-Low-viscosity adhesive 112 connects the inner layer with the inner surface of the glass dome and going up between the fiber and the inner wall of the dome up towards the fused (collapsed) section of the fiber and the dome. A second viscous adhesive 114 connects the outer jacket (nylon) layer with the proximal end of the glass dome/cover. It may be shaped/sanded to improve the smoothness of the transition zone between the outer jacketed fiber and the glass dome shape. One of its primary tasks is to make a very smooth junction between the fiber's outermost coating and the glass dome. This smooth connection(transition) is important to prevent the surrounding human tissue from injuries when the fiber is moved back and forth.

Figure 2:
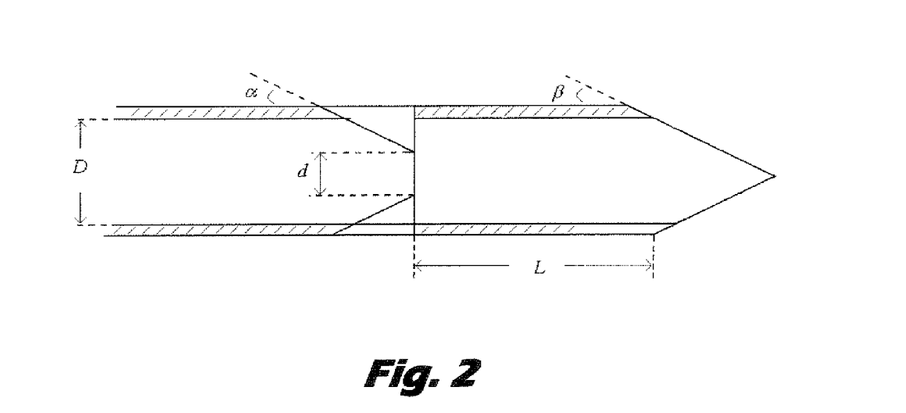
FIG. 2 depicts a preferred embodiment showing dimensional parameters.

FIG. 2 depicts a fiber core portion of present invention showing design parameters which can be modified according to desired results. The angles $\alpha/2$ and $\beta/2$ define the direction into which light is emitted from the conical section of the probe. Additionally, d is the diameter of the truncated cone, D is the fiber core diameter and L is the length of the fiber segment in front of the fiber with its truncated cone. Preferred embodiments have a length L=4, 6, 8 and 10 mm.

The present invention is further illustrated by the following examples, but is not limited thereby. Examples refer to the angle $\alpha$ but would be also valid for $\beta$.

Example 1

Figure 3:
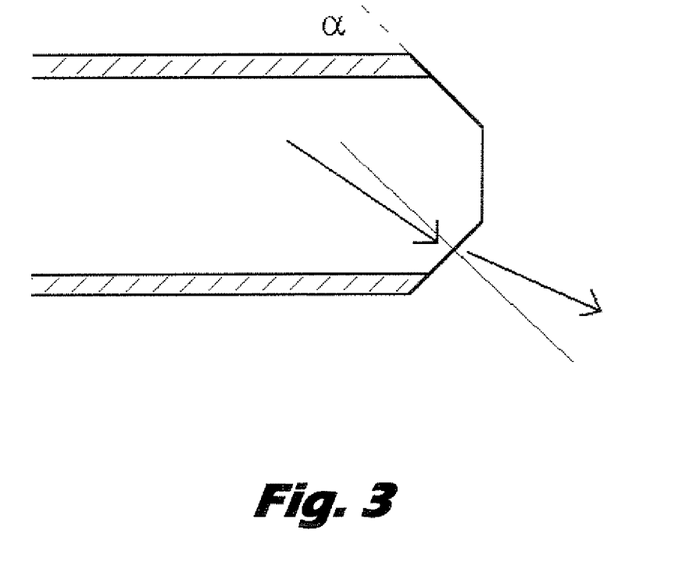
FIG. 3 depicts another preferred embodiment with a large angle α.

FIG. 3 shows a fiber core portion depicting the direction of emission of light at an emission section where the angle $\alpha$ defines the direction into which light is emitted from the conical section of the probe. With this configuration, a large angle $\alpha$ will make the light to be emitted sideways and in forward-direction.

Example 2

Figure 4:
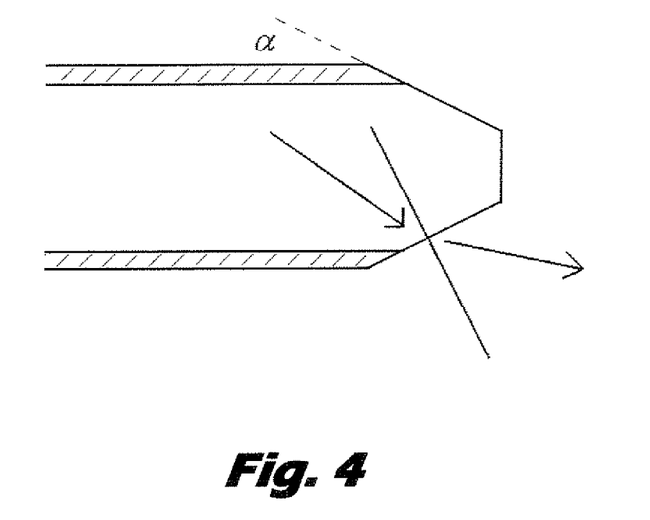
FIG. 4 depicts another preferred embodiment with a small angle α.

FIG. 4 shows another fiber core portion depicting the direction of emitted light at an emission section where the angle $\alpha$ defines the direction into which light is emitted from the conical section of the probe. In this example, a relatively larger angle $\alpha$ in comparison with example 1 will make a larger amount of radiation be emitted in forward direction.

Example 3

Figure 5:
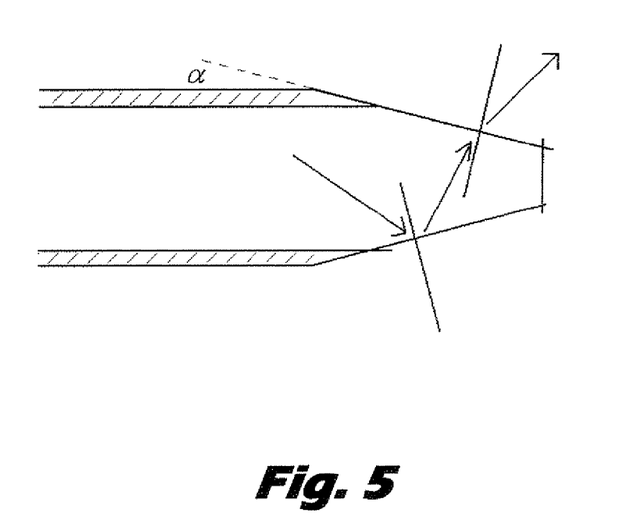
FIG. 5 depicts another preferred embodiment with a small angle α such that total internal reflection occurs.

FIG. 5 shows yet another fiber core portion depicting the direction of emission of light at an emission section where the angle $\alpha$ defines the direction into which light is emitted from the conical section of the probe. In this case, the angle $\alpha$ is small enough to cause total internal reflection. The laser beam "bounces" through the conical section until it is emitted.

Example 4

Figure 6:
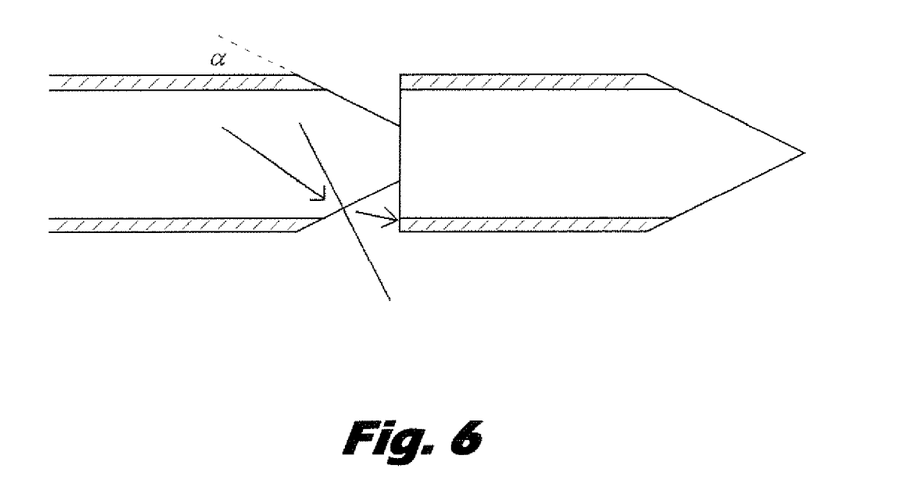
FIG. 6 This FIG. depicts an example of why angle α has to be chosen carefully.

FIG. 6 shows another fiber core portion depicting the direction of emission of light at an emission section where the angle $\alpha$ defines the direction into which light is emitted from the conical section of the probe. This example shows that the angle $\alpha$ has to be chosen carefully. For certain values of $\alpha$, the laser radiation might be emitted in such a direction that it strikes the fiber section in front of the truncated conical section. This could lead to uncontrollable, or unintended reflection and scattering and result in severe damage of the patient's tissue. Some designs though could benefit from controlled, intended reflection from the base of the next section, simply spreading the initial treatment to a larger area.

Example 5

The diameter d of the truncated cone controls the amount of laser radiation that is launched from the fiber with its truncated conical tip into the fiber segment in front of it. If the cross sectional area of the truncated cone $$\left(\frac{\pi d^2}{4}\right)$$

is ⅓ of the fiber core area $$\left(\frac{\pi D^2}{4}\right),$$

the laser power will be split 50:50 between the two conical areas. This has been experimentally confirmed by measuring outputs with and without the contribution of the inline conical diffuser. This simplifies to $d^2/D^2=⅓$, or $d/D=(⅓)^{0.5}$. If the cross sectional area of the truncated core is ½ of the fiber core's area, (or effectively $d^2/D^2=½$) approximately 60-65% of the laser power is launched into the frontal fiber segment. Experiments confirmed that the power splitting could be adjusted with a precision of better than ±10%. It has to be taken into account that multimode fibers do not provide a homogeneous intensity distribution with respect to the core cross section. The transmitted beam has a nearly Gaussian beam profile. Therefore, the ratio of the power splitting between the fiber and the frontal fiber segment is really only approximated by linear correlation with the ratio of the two areas.

Example 6

Figure 7:
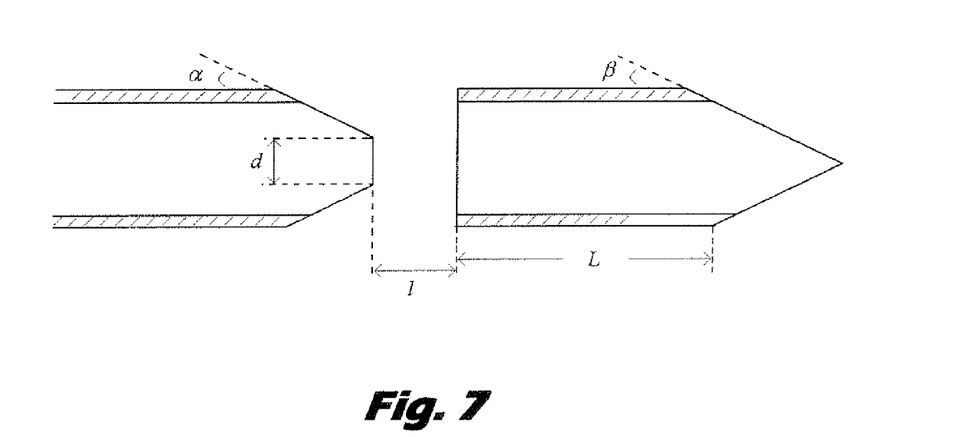
FIG. 7 depicts another preferred embodiment with an air gap.

FIG. 7 depicts another embodiment with fiber core portion of present invention showing design parameters which can be modified according to desired results. The angles $\alpha/2$ and $\beta/2$ define the direction into which light is emitted from the conical section of the probe. Additionally, d is the diameter of the truncated cone, D is the fiber core diameter and L is the length of the fiber segment in front of the fiber with its truncated cone. Preferably, there is a gap of air or liquid with length, l. A very small air gap would enhance mixing the light passing out of the truncated core as it enters the next section, helping to fill in modes for redirection at the conical end surface. A fluid contained in the chamber should be chosen such that it aids the forward travelling beams to enter into the distal section.

Example 7

Figure 8:
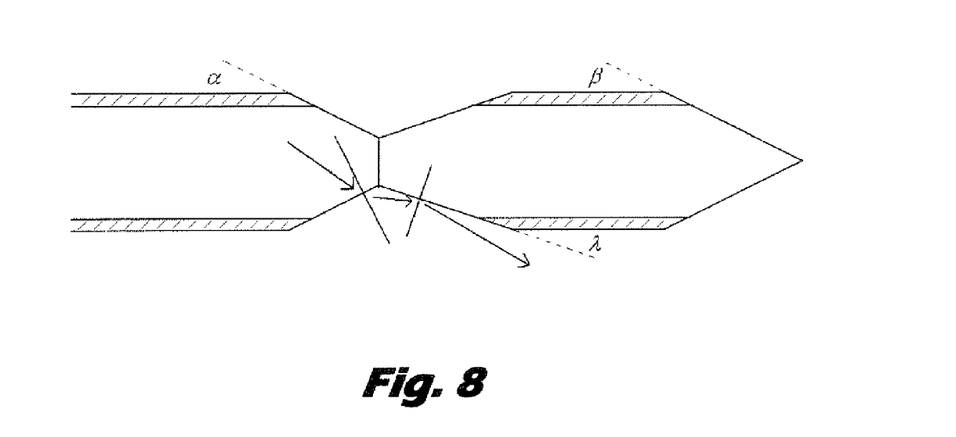
FIG. 8 depicts another preferred embodiment in which the front segment has an additional conical section which is truncated and oriented in backward direction

FIG. 8 shows another variation of before-mentioned examples in which the distal most segment has an additional conical section which is truncated and oriented in backward direction. Its angle is denoted as $\lambda$. This configuration is useful to direct the emitted radiation or to concentrate light in a certain direction. It also captures and reasonably distributes light leaking past the distal cone end.

There are different methods to assemble the fiber with the truncated cone and the short fiber segment with the conical tip in front of the fiber. In a preferred embodiment, the fiber and the fiber segment are "butt-coupled" inside the glass dome with no additional adhering means. As the back end of the truncated cone section is fused to the outer tube, the area in close contact with the forward piece is fused to the forward section. In another preferred embodiment, the truncated cone of the fiber is glued to the proximal end of the fiber segment. Gluing may yield increased attenuation and thus significantly reduced damage threshold, but for low energy treatments, such as vein treatments, it is an alternative, if the glue is chosen properly for its temperature and spectral properties. In yet another embodiment, the contact area is fused, prior to enclosing in the cap section. In all cases, the fiber and the short fiber segment are laterally fused to the protective glass dome. Actually the fiber tip with full cone is put into the glass dome and side fused after a vacuum is drawn on the set and the fusion is similar to a collapsing of a tube over a core rod.

Figure 9:
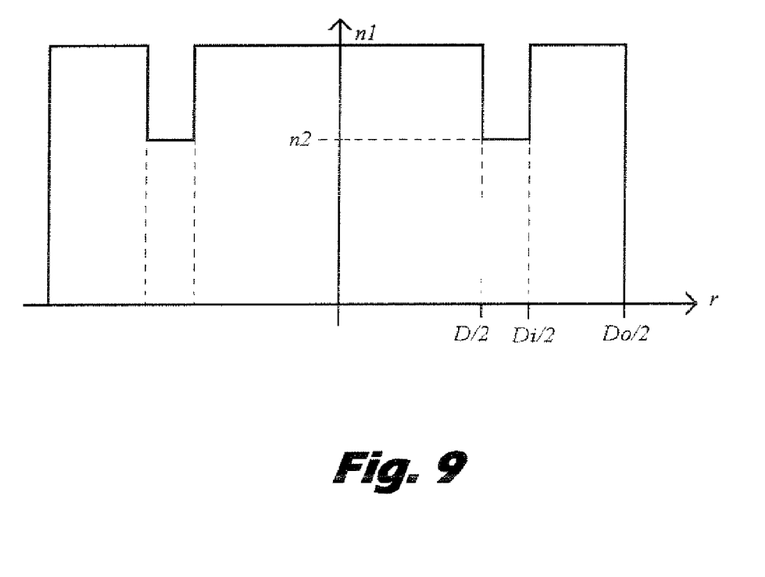
FIG. 9 shows a graph of the refractive index profile of a preferred embodiment.

In a preferred embodiment, manufacturing is achieved from a so-called SWS1.2 preform, a silica/silica clad/core rod, used to draw the respective fibers. The refractive index profile is depicted in FIG. 9. The core has a radius D/2 and a refractive index $n_1$. It is surrounded by a fluorinated layer with a radius $Di/2=1.06 \times D/2$ and a refractive index $n_2$. This fluorinated cladding layer itself is surrounded by an overclad section. Its radius is $Do/2=1.2 \times D/2$. Its refractive index is $n_1$. This section consists of pure silica like the fiber core.

During the draw process, first a plastic hard clad is added with a thickness of approximately 15 µm. Then, this structure is jacketed with two separate layers of plastic materials. The overclad section and the glass dome consist of the same material, therefore they have the same physical, and thermal properties. Thus, they can be fused together with good quality and reasonable mechanical strength. If the outermost glass layer of the fiber was made from fluorinated silica, it would be very likely that bubbles would form during this splicing procedure. Such bubbles reduce/weaken the mechanical strength of the connection of the fiber/fiber segments with the glass dome, as well as compromise optical properties too. This is due to thermal mismatches and fictive temperature and viscosity differences. Moreover, it would lead to additional, uncorrectable scattering as well as optical loss along such sections.

The conical sections on the distal end of a fiber are formed by grinding and polishing techniques. In some embodiments, the size of the abrasive grit is ≥3 µm. In other embodiments, smaller grain size (as small as 0.3 µm) are applied. It was observed, that polishing with abrasive grit with size smaller than 3 µm yields a certain surface roughness. This surface roughness is advantageous as it yields some scattering at the surface of the conical section. This scattering causes an angular distribution of the light which is emitted from the cone. This could be advantageous in medical applications as an expanded area of tissue could be irradiated.

In a preferred embodiment, a number of fibers having conical fiber tips are bundled in a polishing mount. By polishing this fiber bundle perpendicular to the fiber axis, the conical tip is truncated. In another preferred embodiment a number of fibers having conical tips are cleaved in such a way that the resulting fiber sections have the desired length L.

In a preferred embodiment, the coating of the fibers consists of two separate layers of nylon or Tefzel, in any combination: i.e. inner/outer, nylon/nylon, Tefzel/nylon, nylon/Tefzel or Tefzel/Tefzel. The outer layer is quite thick compared to the thickness of the inner layer. These coating layers are removed at different lengths from the distal fiber end. Thus, the inner nylon layer reaches towards the distal end while the outer layer is stopped by the wall of the glass dome. The inner jacketed fiber fits in about 1-4 mm before the bare fiber continues in the glass dome (tube).

Figure 10:
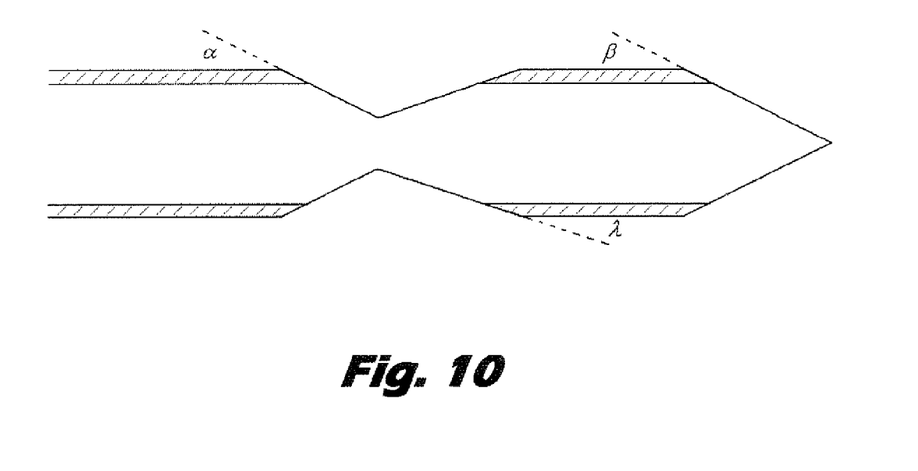
FIGS. 10 and 11 show preferred embodiments that take into account recent developments and improvements in laser material processing of silica.
Figure 11:
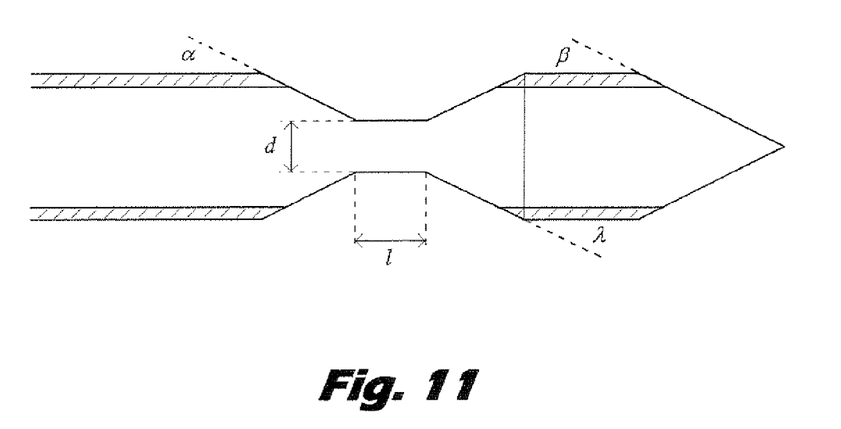

Recent developments and improvements in laser material processing of silica, especially (ultra-) short pulsed lasers allow for drilling, structuring and shaping of silica, yielding surfaces with (nearly) optical quality. FIGS. 10 and 11 show two preferred embodiments that take advantage of such a procedure to a silica fiber. A multi-radial probe is manufactured from a single piece of fiber, i.e. without the necessity to use different discrete segments. Therefore, light is emitted from two or more fiber sections. The truncated cone section can be polished or into a fiber section, as is shown in FIGS. 10 and 11, to keep the entire probe continuous and, thus butt-welding a truncated cone to a small fiber segment is no longer needed.

Optical fiber set disclosed can be used with laser sources and other appropriately focusable beam sources of various wavelengths. In a preferred embodiment, laser wavelengths of 980 nm, 1470 nm, 1950 nm or combinations of these wavelengths in appropriate proportions can be used, for a variety of medical applications.

Numerous advantages arise when performing surgical procedures with the disclosed invention. First of all, effectiveness of procedure is essentially assured. This is because radiation is emitted radially in all directions and therefore entire vessel wall is affected, thus achieving complete closure. Second, since the fiber has multiple emission sections, vein closure can be achieved using lower power density. As a consequence lower energy, faster drawback of optical fiber or both can be applied. Third, as lower energies are used, pain inflicted to patient is minimized and thus anesthesia is no longer needed, except at the point of entry of the needle into the skin. Finally, because the system is so efficient due to mentioned advantages, optical fiber conveys less energy and thus has minimum chance of rupture during use.

Having described preferred embodiments of the invention with reference to the accompanying drawings, it is to be understood that the invention is not limited to the precise embodiments, and that various changes and modifications may be effected therein by skilled in the art without departing from the scope or spirit of the invention as defined in the appended claims.

What is claimed is:

1. A device for endoluminal treatment of a blood vessel, comprising:
    a flexible waveguide defining an elongated axis, a proximal end optically connectable to a source of radiation, and a distal end receivable within the blood vessel;
    wherein the distal end of said flexible waveguide includes at least two, conically-shaped radiation emitting surfaces configured to emit radiation reflected laterally with respect to the elongated axis of the waveguide and around the entire circumference of the waveguide onto a portion of a surrounding wall of said blood vessel in an axially extending annular beam;
    wherein a first one of said at least two, conically-shaped radiation emitting surfaces comprises a conical surface, and a second one of said at least two, conically-shaped radiation emitting surfaces comprises a forward truncated conical section and a backward truncated conical section interfacing the forward truncated conical section; and
    a cap that is fixedly secured and sealed to the waveguide, the cap enclosing said at least two conically-shaped radiation emitting surfaces therein and defining a gas-waveguide interface for each of said at least two radiation emitting surfaces;
    wherein radiation is emitted annularly with respect to the elongated axis of the waveguide through said cap.

2. The device according to claim 1, wherein said waveguide comprises a fiber with a distal end including the forward truncated conical section, followed by a fiber segment with the first one of said at least two, conically-shaped radiation emitting surfaces formed at a distal end of said fiber segment.

3. The device according to claim 2, wherein the forward truncated conical section is configured with an angle and a truncated surface diameter such that a predetermined portion of said radiation continues to travel forward within said fiber segment in contact with the forward truncated conical section and a portion of said radiation is irradiated annularly from the elongated axis of the waveguide at the forward truncated conical section.

4. The device according to claim 2, wherein the backward truncated conical section is formed on a proximal end of said fiber segment.

5. The device according to claim 4, wherein the distal end of said fiber is coupled to the proximal end of said fiber segment inside said cap.

6. The device according to claim 2, wherein the distal end of said fiber is glued to said fiber segment.

7. The device according to claim 2, wherein both said fiber segment and the distal end of said fiber are laterally fused to said cap.

8. The device according to claim 2, wherein said fiber comprises a fiber core made of silica that is surrounded by a fluorinated silica layer, wherein said fluorinated silica layer is surrounded by an overclad section consisting of silica, whose refractive index is the same as the fiber core.

9. The device according to claim 2, wherein said fiber comprises an inner layer and an outer layer, wherein said outer layer connects to said cap's proximal end by an adhesive, and said connection is shaped to improve the smoothness of the transition zone between the outer layer of the fiber and the cap.

10. The device according to claim 1, wherein said waveguide is manufactured from a single piece of fiber comprising a silica core and cladding and said cap is manufactured from silica, whose properties are equivalent to silica composing said fiber core.

11. The device according to claim 1, further comprising at least one laser source that provides laser radiation having a wavelength of 1470 nm±30 nm or 1950 nm±30 nm, and a power no greater than 10 W, wherein the proximal end of the waveguide is optically coupled to said at least one laser source, and wherein the at least two radiation emitting surfaces of the waveguide emit radiation laterally with respect to the elongated axis of the waveguide in an axially-extending, annular pattern onto a surrounding vessel wall.

12. A method for endoluminal treatment of a blood vessel employing a device according to claim 1, comprising the following steps:
    (a) introducing a waveguide into a blood vessel, the waveguide comprising a flexible waveguide defining an elongated axis with a proximal end and a distal end, said distal end including at least two conically-shaped radiating emitting surfaces configured to emit radiation in an axially extending annular beam, wherein a first one of said at least two, conically-shaped radiation emitting surfaces comprises a conical surface, and a second one of said at least two, conically-shaped radiation emitting surfaces comprises a forward truncated conical section and a backward truncated conical section interfacing the forward truncated conical section, and a cap that is fixedly secured and sealed to the waveguide, the cap enclosing said at least two conically-shaped radiation emitting surfaces therein and defining a gas-waveguide interface for each of said at least two radiation emitting surfaces;
    (b) allowing said waveguide to center itself within said blood vessel at a site to be treated;
    (c) transmitting radiation through said waveguide from a laser source;
    (d) emitting radiation laterally with respect to said elongated axis of said waveguide onto a portion of a surrounding vessel wall, and
    (e) withdrawing said waveguide at a preselected speed while it is emitting radiation to provide a desired total dose of radiation to said surrounding vessel wall.

13. The method according to claim 12, wherein the emitting step includes laterally emitting radiation onto a region of the surrounding vessel wall extending throughout an angle of at least 90°.

14. The method according to claim 12, wherein radiation is transmitted at a power no greater than 10 W and said radiation has a wavelength of 1450±30 nm or 1900±30 nm.

15. The method according to claim 12, wherein said withdrawing is performed in a controlled semi-automatic, or automatic way, thereby providing a preselected radiation dose to said vessel's surrounding wall.

16. A device for endoluminal treatment of a blood vessel, comprising:
    a flexible waveguide defining a longitudinal axis, the flexible waveguide having a proximal end optically connectable to a radiation source and a distal end receivable within the blood vessel;

a first radiation emitter formed on a tip of the flexible wave guide at the distal end, the first radiation emitter comprising a conical surface; and a second radiation emitter formed on a circumferential surface of the flexible wave guide at the distal end proximate the tip, the second radiation emitter comprising a forward truncated conical section and a backward truncated conical section;

wherein the first and second radiation emitters are configured to emit radiation circumferentially with respect to the longitudinal axis.

17. The device of claim 16, wherein an interface of the forward truncated conical section and the backward truncated conical section defines a cross sectional area having a diameter less than that of the flexible waveguide.

18. The device of claim 16, wherein the first radiation emitter is configured to emit a first fraction of the radiation, and the second radiation emitter is configured to emit a second fraction of the radiation, the first fraction substantially equaling the second fraction.

19. The device of claim 16, wherein the first radiation emitter is configured to emit a first fraction of the radiation, and the second radiation emitter is configured to emit a second fraction of the radiation, the first fraction being greater than the second fraction.

* * * * *